United States Patent [19]

Tafur

[11] Patent Number: 4,937,890

[45] Date of Patent: Jul. 3, 1990

[54] FLAT FOLDED DISPOSABLE FEMALE URINARY AID

[76] Inventor: Jose J. Tafur, 2122 Haven House, Spring, Tex. 77386

[21] Appl. No.: 417,716

[22] Filed: Oct. 5, 1989

[51] Int. Cl.$^5$ .......................................... A47K 11/00
[52] U.S. Cl. ...................................... 4/144.4; 4/144.1;
        4/144.2; 4/144.3; 604/329; 604/347; 604/350
[58] Field of Search .............................. 4/144.1–144.4,
        4/301, 114.1, 450, 454, 463, 456, 455, 452, 462;
                604/329–331, 350, 347, 349; 128/761, 766

[56] References Cited

U.S. PATENT DOCUMENTS

| | | | |
|---|---|---|---|
| 2,878,486 | 3/1959 | Bartlett et al. | 4/144.4 |
| 3,099,017 | 7/1963 | Sullivan | 4/144.2 |
| 3,572,318 | 3/1971 | Garland | 4/144.3 X |
| 3,613,122 | 10/1971 | Gross et al. | 4/144.4 |
| 3,746,240 | 7/1973 | Flynn | 4/144.2 X |
| 3,964,111 | 6/1976 | Packer | 4/144.4 |
| 4,023,216 | 5/1977 | Li | 4/144.3 |
| 4,675,012 | 6/1987 | Rooyakkers | 604/349 |
| 4,681,573 | 7/1987 | McGovern et al. | 4/144.3 X |
| 4,751,751 | 6/1988 | Reno | 4/144.4 |
| 4,815,151 | 3/1989 | Ball | 4/144.4 |
| 4,857,064 | 8/1989 | Mendoza | 604/347 |

FOREIGN PATENT DOCUMENTS 158602  10/1985  European Pat. Off. ............ 604/347

*Primary Examiner*—Henry K. Artis
*Attorney, Agent, or Firm*—Kenneth A. Roddy

[57] ABSTRACT

A flat-folded expandable urinary aid for use by females which allows them to urinate from a standing position has an elongate flat-folded tubular portion terminating at an outlet end and a flat-folded funnel-shaped portion extending outwardly and rearwardly from the opposite end of the tubular portion terminating at an inlet end. The tubular portion and funnel-shaped portions are formed by a pair of opposed planar side walls hinged together from the inlet end to the outlet end along their top and bottom longitudinal edges. The side walls of the funnel-shaped portion are scored or creased along a pair of lines converging angularly from the juncture of the funnel-shaped portion with the tubular portion to intersect at a point approximately one-half the length of the funnel-shaped portion. The side walls of the tubular portion and funnel-shaped portion are creased or scored intermediate its longitudinal edges along a line extending longitudinally from the outlet end to the intersection of the converging score lines. Upon compression of the top and bottom longitudinal edges toward each other, the opposed side walls expand laterally outward from a flat-folded configuration to draw the funnel-shaped portion into a substantially elliptical shaped opening at the inlet end and the tubular portion into a generally diamond shaped configuration having a central opening extending the length of the tubular portion. The elliptical shaped opening at the inlet end is configured to surround the labia major of the user.

15 Claims, 3 Drawing Sheets

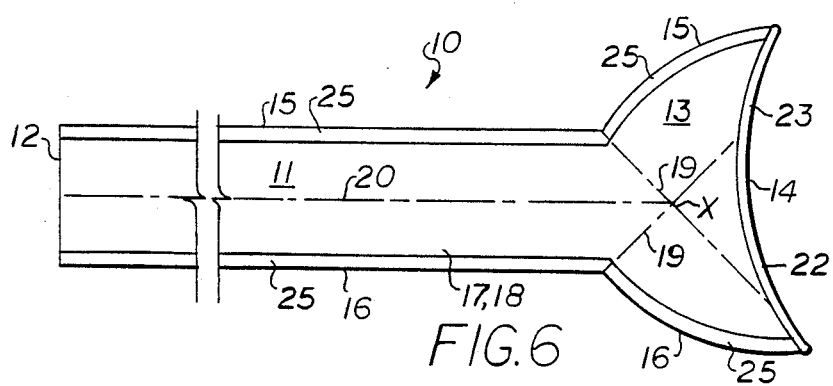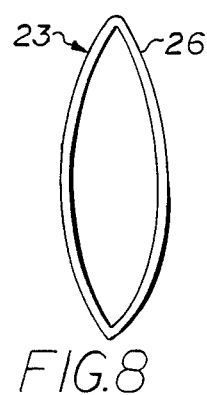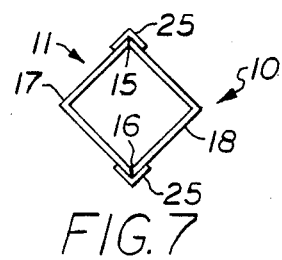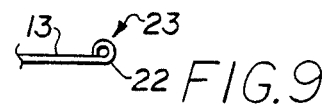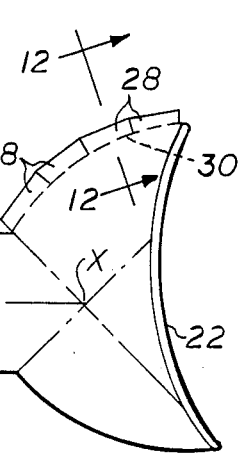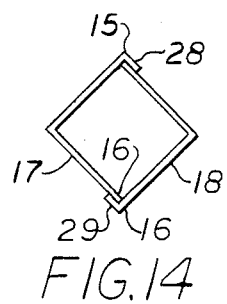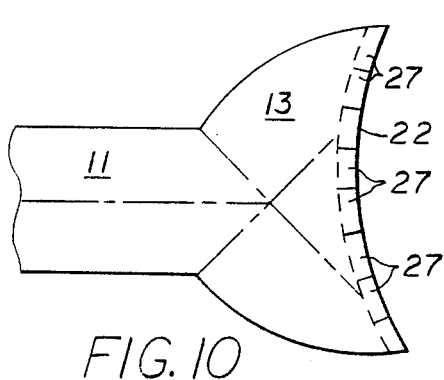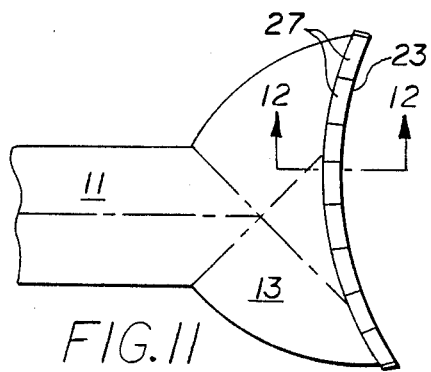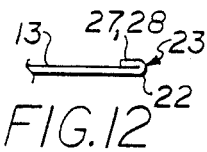

FLAT FOLDED DISPOSABLE FEMALE URINARY AID

BACKGROUND OF THE INVENTION

1. Field of the Invention

This invention relates generally to improvements in feminine hygienic devices, and more particularly to a flat-folded expandable urinary aid for use by females which expands laterally to form a substantially elliptical shaped opening at the inlet end to surround the labia major of the user and a tubular portion having a central opening extending its length which allows them to urinate from a standing position.

2. Brief Description of the Prior Art

Women's public restrooms are most often unclean or unsanitary. In camping and traveling, a restroom is not always convenient or may be non-existant. The desirability of a urinary aid which allows females to urinate from a standing position has been recognized for some time, and numerous devices have been proposed in the art. There are several patents which disclose various urinary aids, most of which are complex constructions which are difficult to erect to the operational configuration and awkward to use.

Garland, U.S. Pat. No. 3,572,318 discloses a funnel-shaped urine specimen collection aid comprising a collapsible funnel structure which has a stabilizer flap for attaching and positioning the device in the mouth of a container during the taking of a urine specimen.

McGovern et al, U.S. Pat. No. 4,681,573 discloses an oblique conical urinary device formed from a flat blank. In one embodiment, the device is curved with the side edges overlapped to form a simple oblique cone shape having a small diameter bottom end and a larger truncated diameter top end. In another embodiment the device has creases and is folded to form a rectangular funnel-shape with angularly opposed side walls and top and bottom walls, and in a third embodiment, is provided with a handle portion.

DeWitt et al, U.S. Pat. No. 4,734,941 discloses a urine conducting appliance comprising a flexible layered sheet adapted to be folded in a U-shape to fit between the legs of a female and direct urine to an appropriate receptacle Zieve et al, U.S. Pat. No. 4,756,029 discloses a flat flexible pad having a hingedly attached flap with expandable side walls to permit the flap to move to an open expanded position forming a conduit for the passing of urine.

Towfigh, U.S. Pat. No. 4,608,046 discloses a urinary aid in the form of a flat folded tubular member which expands when the fold lines are squeezed together. The ends are cut in an S-shape such that either end may be used as the inlet or outlet. In the expanded condition, the cross-sectional configuration changes along its length from a somewhat eliptical or circular shape at the inlet end to a more oblate oval or eliptical shape at the outlet end. The device requires the user to spread the labia and insert the device between the labia in the flat folded condition toward and against the urinary meatus and then squeeze the fold lines together causing the side walls to expand radially outward.

The present invention is distinguished over the prior art in general, and these patents in particular by a flat-folded expandable urinary aid for use by females which has an elongate flat-folded tubular portion terminating at an outlet end and a flat-folded funnel-shaped portion extending outwardly and rearwardly from the opposite end of the tubular portion terminating at an inlet end. The tubular portion and funnel-shaped portions are formed by a pair of opposed planar side walls hinged together from the inlet end to the outlet end along their top and bottom longitudinal edges. The side walls of the funnel-shaped portion are scored or creased along a pair of lines converging angularly from the juncture of the funnel-shaped portion with the tubular portion to intersect at a point approximately one-half the length of the funnel-shaped portion. The side walls of the tubular portion and funnel-shaped portion are creased or scored intermediate its longitudinal edges along a line extending longitudinally from the outlet end to the intersection of the converging score lines. Upon compression of the top and bottom longitudinal edges toward each other, the opposed side walls expand laterally outward from a flat-folded configuration to draws the funnel-shaped portion into a substantially elliptical shaped opening at the inlet end and the tubular portion into a generally diamond shaped configuration having a central opening extending the length of the tubular portion. The elliptical shaped opening at the inlet end is configured to surround the labia major of the user.

SUMMARY OF THE INVENTION

It is therefore an object of the present invention to provide an expandable urinary aid for use by females which allows them to urinate from a standing position.

It is another object of this invention to provide an expandable urinary aid for use by females which expands to form a substantially elliptical shaped opening at the inlet end to surround the labia major of the user and a tubular portion having a central opening extending its length which allows them to direct the urine stream forwardly and away from the user.

Another object of this invention is to provide an expandable urinary aid for use by females having a funnel-shaped inlet end which is curved in the expanded position to reduce splashing and turbulence and facilitates channeling of the urine stream into the tubular portion.

Another object of this invention is to provide an expandable urinary aid for use by females having a funnel-shaped inlet end with an elliptical opening which has a peripheral rounded rim surrounding the opening.

Another object of this invention is to provide an expandable urinary aid for use by females which in its folded condition is easily carried in the purse or pocket.

A further object of this invention is to provide an expandable urinary aid for use by females which may be packaged in quantities in a compact container.

A still further object of this invention is to provide an expandable urinary aid for use by females which is simple in construction, economical to manufacture, and rugged and durable in use.

Other objects of the invention will become apparent from time to time throughout the specification and claims as hereinafter related.

The above noted objects and other objects of the invention are accomplished by a flat-folded expandable urinary aid for use by females which has an elongate flat-folded tubular portion terminating at an outlet end and a flat-folded funnel-shaped portion extending outwardly and rearwardly from the opposite end of the tubular portion terminating at an inlet end. The tubular portion and funnel-shaped portions are formed by a pair of opposed planar side walls hinged together from the inlet end to the outlet end along their top and bottom longitudinal edges. The side walls of the funnel-shaped portion are scored or creased along a pair of lines converging angularly from the juncture of the funnel-shaped portion with the tubular portion to intersect at a point approximately one-half the length of the funnel-shaped portion. The side walls of the tubular portion and funnel-shaped portion are creased or scored intermediate its longitudinal edges along a line extending longitudinally from the outlet end to the intersection of the converging score lines. Upon compression of the top and bottom longitudinal edges toward each other, the opposed side walls expand laterally outward from a flat-folded configuration to draws the funnel-shaped portion into a substantially elliptical shaped opening at the inlet end and the tubular portion into a generally diamond shaped configuration having a central opening extending the length of the tubular portion. The elliptical shaped opening at the inlet end is configured to surround the labia major of the user.

BRIEF DESCRIPTION OF THE DRAWINGS

FIG. 6 is a side elevation of an embodiment of the urinary aid having side walls hinged together with tape.

FIG. 7 is a transverse cross section through the tubular portion of the embodiment of FIG. 6 in the expanded condition.

FIG. 8 is a front elevation of a looped rim element to be installed on the rearward edge of the funnel-shaped portion.

FIG. 9 is a fragmentary cross section of a rounded rim formed on the rearward edge of the funnel-shaped portion.

FIGS. 10 and 11 are partial side elevations of an embodiment of the urinary aid having a rim formed by folded tabs on the rearward edge of the funnel-shaped portion.

FIG. 12 is a fragmentary cross section of the rim formed by tabs on the rearward edge of the funnel-shaped portion taken along line 12 of FIG. 11.

FIG. 13 is a side elevation of an embodiment of the urinary aid having side walls hinged together with tabs along the longitudinal edges.

FIG. 14 is a transverse cross section through the tubular portion of the embodiment of FIG. 13 in the expanded condition.

DESCRIPTION OF THE PREFERRED EMBODIMENT

Figure 1:
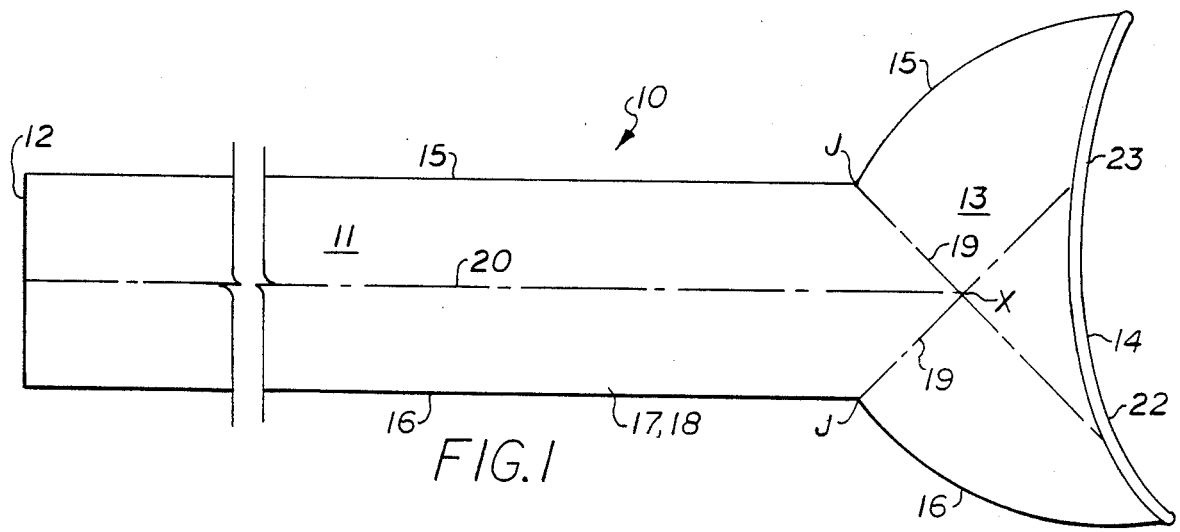
FIG. 1 is a side elevation of a preferred expandable urinary aid for feminine use in accordance with the present invention shown in the flat condition.
Figure 2:
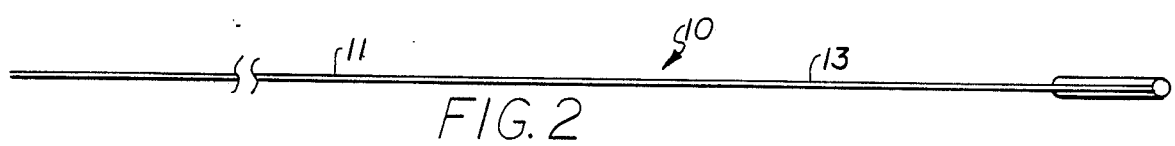
FIG. 2 is a bottom plan view along the longitudinal edge of the urinary aid of FIG. 1 shown in the flat condition.

Referring to the drawings by numerals of reference, there is shown in FIGS. 1-5, a preferred expandable urinary aid 10 for feminine use. The device 10 is made from a foldable, disposable, biodegradable, and at least temporarily waterproof material, such as certain types of paper or light cardboard material.

The device 10 has an elongate flat-folded tubular portion 11 terminating at an outlet end 12 and a flat-folded funnel-shaped portion 13 extending outwardly and rearwardly from the opposite end of the tubular portion terminating at an inlet end 14. As explained in detail hereinafter, the tubular portion 11 and funnel-shaped portion 13 are formed from two sheets of material which are hinged together from the inlet end 14 to the outlet end 12 along their top and bottom longitudinal edges 15 and 16, respectively to form a pair of opposed planar side walls 17 and 18.

As represented by phantom lines in FIG. 1, each planar side wall 17 and 18 of the funnel-shaped portion 13 is creased or scored on its surface along a pair of lines 19 converging angularly from the juncture J of the top and bottom edges of the funnel-shaped portion 13 with the top and bottom edges of the tubular portion 11 and intersecting at a point X approximately one-half the length of the funnel-shaped portion 13. Each planar side wall 17 and 18 of the tubular portion and the funnel-shaped portion is also creased or scored on its surface intermediate its top and bottom longitudinal edges 15 and 16 along a line 20 extending longitudinally from the outlet end 12 and terminating at the intersection X of the converging score lines 19.

Figure 3:
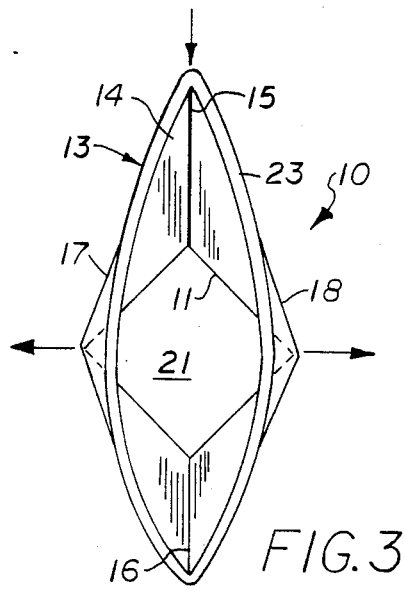
FIG. 3 is an elevation view looking into the inlet end of the urinary aid in the expanded condition.
Figure 4:
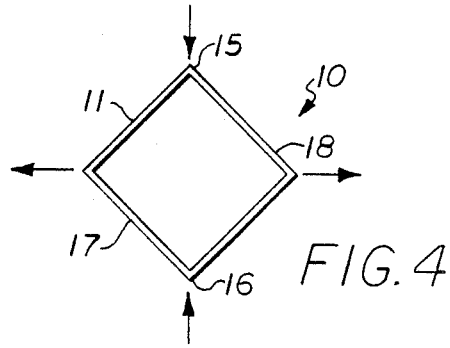
FIG. 4 is a transverse cross section through the tubular portion of the urinary aid in the expanded condition.

As shown in FIGS. 3 and 4, the opposed creased or scored side walls 17 and 18 will expand laterally outward along the crease or score lines 19 and 20 from a flat-folded configuration to define a central longitudinal opening 21 in response to compression of the top and bottom longitudinal edges 15 and 16 toward each other.

The cross sectional configuration of the opposed planer side walls 17 and 18 in the laterally outward expanded position (FIGS. 3 and 4) draws the funnel-shaped portion 13 into a substantially elliptical shaped opening at the inlet end and the tubular portion 11 into a generally diamond shaped opening 21 extending the length of the tubular portion.

Figure 5:
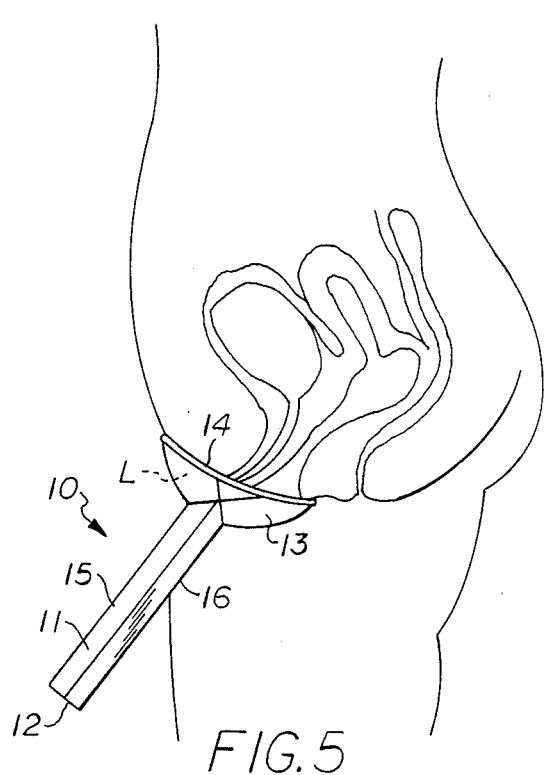
FIG. 5 is a fragmentary side elevation showing the urinary aid in relation to the feminine body during urination.

Referring additionally to FIG. 5, the substantially elliptical shaped opening thus formed at the inlet end 14 of the funnel-shaped portion 13 is configured to surround the labia major L of the user.

To facilitate an optimum fit around the labia major L, the rearward edge 22 of each said planar side wall of the funnel-shaped portion 13 is curved arcuately inward. Thus, in the expanded condition, the outer edge 22 of the substantially elliptical shaped opening of the funnel-shaped portion 13 will also be curved inwardly closely following the body contour of the user whereby the funnel-shaped portion 13 may adjustably moved to provide a preferred angular position of the tubular portion 11 to facilitate direction of the urine stream forwardly and away from the user (FIG. 5).

The top and bottom longitudinal edges 15 and 16 of the planar side walls 17 and 18 of the funnel-shaped portion 13 may also be curved outwardly and rearwardly in opposed relation from their junction J with the longitudinal edges of the tubular portion 11 whereby the curved top and bottom edges of the funnel-shaped portion in the laterally outward expanded position reduces splashing and turbulence and facilitates channeling of the urine stream into the opening 21 of the tubular portion 11. The diamond-shaped opening 21 through the tubular portion 11 also facilitates drainage of the urine.

Depending upon the material used for the device, the rearward edge 22 of the funnel-shaped portion 13 may be provided with a rim 23 which forms a peripheral rim surrounding the elliptical opening when the device is in the expanded position to provide a comfortable fit against the body of the user.

FIGS. 6–13 illustrate various methods of constructing the urinary aid. As seen in FIGS. 6 and 7, the device 10 may be constructed from two pieces of suitable paper or light cardboard material which are cut in the shape described above and shown in FIG. 1 and provided with the previously described crease or score lines 19 and 20. The two pieces are placed together to form the opposing planar side walls 17 and 18 and hingedly joined together by strips of flexible tape 25 secured along their top and bottom longitudinal edges 15 and 16.

As shown in FIG. 8, the rim 23 may be a separate piece of soft material, such as cord, formed in a loop 26 and glued or otherwise conventionally secured to the rearward edge 22 of the funnel-shaped portion 13. The rim 23 may also be formed by rounding the rearward edge 22 over itself in the manner of a lip of a paper cup (FIG. 9). The rim 23 may also be formed by cutting the rearward edge 22 of the funnel-shaped portion 13 material to have outwardly extending tabs 27 at the rearward end and creasing or scoring the tabs 27 along the rearward edge 22 such that they may be folded and secured back upon the side wall to form a double ply of the material (FIGS. 10–12).

As shown in FIGS. 13 and 14, the device 10 may also be constructed from two pieces of suitable paper or light cardboard material which are cut in the shape described above and shown in FIG. 1. One piece 17 would be provided with tabs 28 which extend outwardly from the top longitudinal edge 15 and the other piece 18 provided with tabs 29 which extend outward from its bottom longitudinal edge 16. The two pieces would be creased or scored along fold lines 30 (dashed lines). The two pieces 17 and 18 would then be placed together to form the opposing planer side walls 17 and 18 and the tabs 28 and 29 folded over and glued to the opposing side wall to join the side walls 17 and 18 together (FIG. 14).

Figure 15:
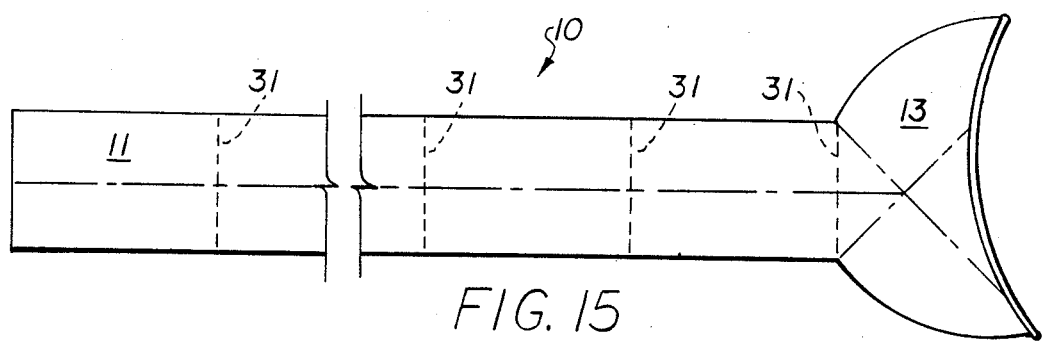
FIGS. 15 and 16 are side and edge views, respectively, illustrating how the urinary aids may be folded for packaging.
Figure 16:
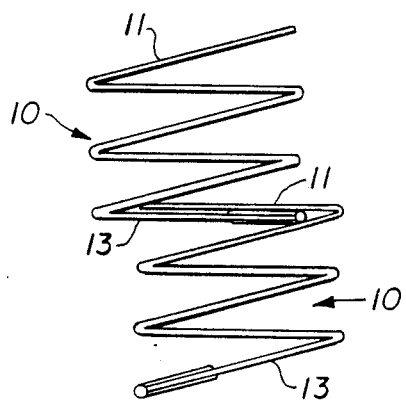
Figure 17:
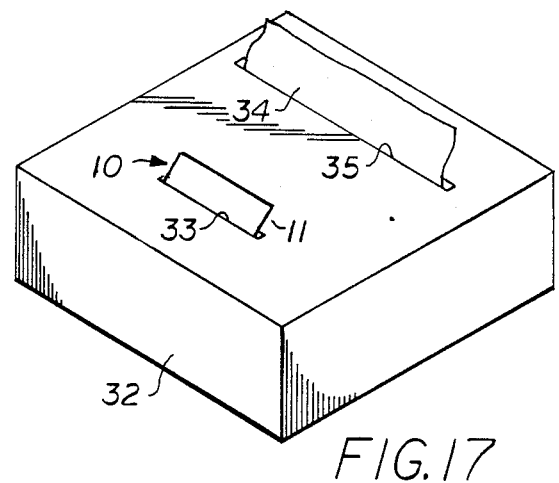
FIG. 17 is an isometric illustration of a dispensing container having a plurality of urinary aids and tissues contained therein.

FIGS. 15–17 illustrate a method of packaging and dispensing the urinary aids 10. The tubular portion of each device 10 is transversly folded along its length at fold lines 31 in a zig-zag or accordian folded configuration. The outermost tubular portion 11 of one device is inserted into the fold above the funnel-shaped portion 13 of another device as the folded devices are stacked one on top of another. The stacked devices 10 may then be packaged in a container 32 which is slotted at the top. The tubular portion 11 of the uppermost device is pulled through the slot 33 of the container 32. As the top urinary aid 10 is pulled from the container, the tubular portion of the next lower one will be positioned in the slot 33. The container 32 may also contain a supply of tissues 34 which are similarly dispensed from another slot 35.

OPERATION

To use the urinary aid 10, the user takes one from its package and unfolds it to an elongate flat configuration. Holding the device with the thumb on the top edge 15 and a finger on the bottom edge 13 near the juncture J of the tubular portion with the funnel-shaped portion, the user gently squeezes the top and bottom edges toward each other.

As shown in FIGS. 3 and 4, responsive to the squeezing action, the opposed creased or scored side walls 17 and 18 will expand laterally outward along the crease or score lines 19 and 20 from a flat-folded configuration to define a central longitudinal opening 21 through the tubular portion 11. The cross sectional configuration of the opposed planer side walls 17 and 18 in the laterally outward expanded position draws the funnel-shaped portion 13 into a substantially elliptical shaped opening at the inlet end and the tubular portion 11 into a generally diamond shaped opening 21 extending the length of the tubular portion.

Referring additionally to FIG. 5, the substantially elliptical shaped opening thus formed at the inlet end 14 of the funnel-shaped portion 13 is positioned to surround the labia major L of the user. The curved outer edge 22 of the elliptical shaped opening of the funnel-shaped portion 13 will closely following the body contour of the user and the funnel-shaped portion 13 may adjustably moved to provide a preferred angular position of the tubular portion 11 to facilitate direction of the urine stream forwardly and away from the user. After use, the urinary aid may be flushed down the toilet or disposed of in a convenient trash container.

While this invention has been described fully and completely with special emphasis upon a preferred embodiment, it should be understood that within the scope of the appended claims the invention may be practiced otherwise than as specifically described herein.

I claim:
1. An elongate flat-folded expandable urinary aid for feminine use comprising;
   an elongate flat-folded tubular portion terminating at an outlet end, and
   a flat-folded funnel-shaped portion extending outwardly and rearwardly from the opposite end of said tubular portion terminating at an inlet end,
   said flat-folded tubular portion and said funnel-shaped portion defined by a pair of opposed planar side walls hinged together from said inlet end to said outlet end along their top and bottom longitudinal edges,
   each said planar side wall of said funnel-shaped portion being scored on its surface along a pair of lines converging angularly from the juncture of said funnel-shaped portion longitudinal edges with said tubular portion longitudinal edges to intersect at a point approximately one-half the length of said funnel-shaped portion, and
   each said planar side wall of said tubular portion and said funnel-shaped portion being creased or scored on its surface intermediate its longitudinal edges along a line extending longitudinally from said outlet end and terminating at the intersection of said converging score lines, whereby
   said opposed planar side walls expand laterally outward from a flat-folded configuration to define a central longitudinal opening in response to com- pression of the top and bottom longitudinal edges toward each other.

2. A urinary aid according to claim 1 wherein the cross sectional configuration of said opposed planer side walls in the laterally outward expanded position draws said funnel-shaped portion into a substantially elliptical shaped opening at the inlet end and said tubular portion into a generally diamond shaped opening extending the length of said tubular portion.

3. A urinary aid according to claim 2 wherein said substantially elliptical shaped opening at the inlet end of said funnel-shaped portion is configured to surround the labia major of the user.

4. A urinary aid according to claim 3 wherein the rearward edge of each said planar side wall of said funnel-shaped portion is curved arcuately inward, and
said opposed planer side walls in the laterally outward expanded position draws said funnel-shaped portion into a substantially elliptical shaped opening curved inwardly at the inlet end, whereby
said inwardly curved portion may be adjustably positioned surrounding the labia major to facilitate direction of the urine stream forwardly and away from the user.

5. A urinary aid according to claim 3 wherein the top and bottom longitudinal edges of each said planar side wall of said funnel shaped portion are curved outwardly and rearwardly in opposed relation from their juncture with the longitudinal edges of said tubular portion, whereby
said curved top and bottom edges of said funnel-shaped portion in the laterally outward expanded position reduces splashing and turbulence and facilitates channeling of the urine stream into said tubular portion.

6. A urinary aid according to claim 3 including a rounded rim at the rearward edge of said planar side walls of said funnel-shaped portion adapted to form a peripheral rim surrounding said elliptical opening in said expanded position.

7. A urinary aid according to claim 6 wherein said rim is a separate piece of soft material formed in a loop and secured to said rearward edge of said funnel-shaped portion.

8. A urinary aid according to claim 6 wherein said rim is an integral portion of said rearward edge which is rounded over itself to form a rounded lip.

9. A urinary aid according to claim 6 wherein said rim is formed by tabs which extend outwardly beyond said funnel-shaped portion rearward edge and which are folded along said rearward edge and secured back upon said funnel-shaped portion side wall to form a double ply of the side wall material.

10. A urinary aid according to claim 3 wherein the rearward edge of each said planar side wall of said funnel-shaped portion is curved arcuately inward and provided with a rim on the curved portion, and
said opposed planer side walls in the laterally outward expanded position draws said funnel-shaped portion into a substantially elliptical shaped opening curved inwardly and having a peripheral rim at the inlet end, whereby
said inwardly curved portion may be adjustably positioned surrounding the labia major to facilitate direction of the urine stream forwardly and away from the user and to provide a comfortable fit against the body of the user.

11. A urinary aid according to claim 1 wherein said elongate flat-folded tubular portion and said flat-folded funnel-shaped portion planer side walls are hingedly joined together by strips of flexible tape secured along their top and bottom longitudinal edges.

12. A urinary aid according to claim 1 wherein said side walls are formed of two pieces of material, one of which having foldable tabs extending outwardly beyond its top longitudinal edge and the other of which having foldable tabs extending outward beyond its bottom longitudinal edge,
said two pieces assembled together with said tabs in opposed relation, and
said tabs of one piece folded over the longitudinal edge of the other piece and secured to the opposing side wall to hingedly join said pieces together.

13. A urinary aid according to claim 1 including a compact container for receiving a plurality of said urinary aids, and
a plurality of said urinary aids are folded transversly along the length of their said tubular portions in a generally Z-shaped configuration and contained in a stacked folded condition within said compact container having a slotted opening.

14. A urinary aid according to claim 13 wherein said plurality of transversly folded urinary aids are assembled in the stacked condition with the outermost tubular portion of one urinary aid received in the folds of another, whereby
upon said tubular portion of the uppermost urinary aid being pulled through the slotted opening of the container, said tubular portion of the next lower urinary aid will be extended partially outwardly from the slotted opening in the container.

15. A urinary aid according to claim 14 including a supply of tissues folded and contained in a stacked condition within said container,
said container having another slotted opening for dispensing said tissues,
said tissues being folded and assembled in the stacked condition with edge of one tissue received in the folds of another, whereby
upon the uppermost tissue being pulled through the slotted opening of the container, the next lower tissue will be extended partially outwardly from the second slotted opening in the container.

* * * * *